(12) United States Patent
Banin et al.

(10) Patent No.: US 8,774,936 B2
(45) Date of Patent: Jul. 8, 2014

(54) PHOTOELECTRICAL DEVICES FOR STIMULATING NEURONS

(75) Inventors: Uri Banin, Mevasseret Zion (IL); Shlomo Yitzchaik, Jerusalem (IL); Ori Cheshnovsky, R'anana (IL); Yael Hanein, Cesarea (IL); Evelyne Sernagor, Newcastle upon Tyne (GB)

(73) Assignees: Yissum Research Development Company of the Hebrew University of Jerusalem, Ltd., Jerusalem (IL); Ramot at Tel-Aviv University Ltd., Tel Aviv (IL)

( * ) Notice: Subject to any disclaimer, the term of this patent is extended or adjusted under 35 U.S.C. 154(b) by 174 days.

(21) Appl. No.: 13/384,654

(22) PCT Filed: Jul. 20, 2010

(86) PCT No.: PCT/IL2010/000574
§ 371 (c)(1),
(2), (4) Date: Apr. 20, 2012

(87) PCT Pub. No.: WO2011/010305
PCT Pub. Date: Jan. 27, 2011

(65) Prior Publication Data
US 2012/0197364 A1 Aug. 2, 2012

Related U.S. Application Data

(60) Provisional application No. 61/227,472, filed on Jul. 22, 2009.

(51) Int. Cl.
*A61N 1/05* (2006.01)
*A61N 1/36* (2006.01)

(52) U.S. Cl.
CPC .......... *A61N 1/0543* (2013.01); *A61N 1/36046* (2013.01)
USPC ........................................................ 607/115

(58) Field of Classification Search
USPC ..................................... 607/88, 116; 600/395
See application file for complete search history.

(56) References Cited

U.S. PATENT DOCUMENTS

| | | |
|---|---|---|
| 2006/0129210 A1 | 6/2006 | Cantin et al. |
| 2006/0272701 A1 | 12/2006 | Ajayan et al. |
| 2007/0123766 A1 | 5/2007 | Whalen, III et al. |
| 2010/0211146 A1 | 8/2010 | Strowbridge et al. |

OTHER PUBLICATIONS

Zhang et al., "Multimodal fast optical interrogation of neural circuitry," *Nature*, vol. 446, Apr. 5, 2007, pp. 633-641.

(Continued)

*Primary Examiner* — Carl H Layno
*Assistant Examiner* — Jon Eric C Morales
(74) *Attorney, Agent, or Firm* — Oliff PLC

(57) ABSTRACT

The present invention provides a novel photoelectrical device for efficient transmission of electrical signals to a neuron. This photoelectrical device comprises one or more charging units for coupling to and stimulating one or more neurons by charge, the charging unit comprising: a nanostructure-based electrode having a surface, which has a predetermined developed surface area for coupling to a neuron and which carries a plurality of photosensitive regions (e.g. quantum dots) interfacing with a biocompatible macromolecule for tuning the relative energy levels between the photosensitive regions and the electrode, as well as for directing the spatial polarity of charge separation the surface being thereby electrically chargeable and dischargeable in response to light excitation of the photosensitive regions, the charges stimulating the neuron when coupled to the surface.

32 Claims, 12 Drawing Sheets

(56) References Cited

OTHER PUBLICATIONS

Berndt at al., "Bi-stable neural state switches," *Nature Neuroscience*, vol. 12, No. 2, Feb. 2009, pp. 229-234.

Pappas at al., "Nanoscale Engineering of a Cellular Interface with Semiconductor Nanoparticle Films for Photoelectric Stimulation of Neurons," *Nano Letters*, vol. 7, No. 2, 2007, pp. 513-519.

Winter et al., "Quantum dots for electrical stimulation of neural cells," *Proceedings of the SPIE—The International Society for Optical Engineering*, vol. 5705, 2005, pp. 235-246.

http://www.photonies.com/Article.aspx?AID=33995, "Quantum Dots Move Beyond Flourescence Imaging." Jun. 1, 2008.

Alivisatos, "The use of nanocrystais in biological detection," *Nature Biotechnology*, vol. 22, No. 1, Jan. 2004, pp. 47-52.

Schroeder at al., "Folate-mediated tumor cell uptake of quantum dots entrapped in lipid nanoparticles," *Journal of Controlled Release*, vol. 124, 2007, pp. 28-34.

Winter et al., "Recognition Molecule Directed Interfacing Between Semiconductor Quantum Dots and Nerve Cells," *Advanced Materials*, vol. 13, No. 22, Nov. 16, 2001, pp. 1673-1677.

Juárez et al., "Quantum Dot Attachment and Morphology Control by Carbon Nanotubes," *Nano Letters*, vol. 7, No. 12, 2007, pp. 3564-3568.

Ben-Jacob et al., "Carbon nanotube micro-electrodes for neuronal interfacing," *Journal of Materials Chemistry*, vol. 18, 2008, pp. 5181-5186.

Gabay et al., "Electro-chemical and biological properties of carbon nanotube based multi-electrode arrays," *Nanotechnology*, vol. 18, 2007, 035201, pp. 1-6.

Oren et al., "Electrically conductive 2D-PAN-containing surfaces as a culturing substrate for neurons," *J. Biomater. Sci. Polymer Edn.*, vol. 15, No. 11, 2004, pp. 1355-1374.

Medintz et al., "Quantum dot bioconjugates for imaging, labelling and sensing," *Nature Materials*, vol. 4, Jun. 2005, pp. 435-446.

David-Pur et al., "Very Low Impedance Micro/Nano Electrodes," *Eurosensors*, 2008.

Sorkin et al., "Process entanglement as a neuronal anchorage mechanism to rough surfaces," *Nanotechnology*, vol. 20, 2009, pp. 1-8.

Gao et al., "CdTe Quantum Dots-Sensitized $TiO_2$ Nanotube Array Photoelectrodes", *J. Phys. Chem.*, vol. 113, Apr. 8, 2009, pp. 7531-7535.

Sun et al., "CdS Quantum Dots Sensitized $TiO_2$ Nanotube-Array Photoelectrodes" *J. Am. Chem. Soc.*, vol. 130, Jan. 10, 2008, pp. 1124-1125.

Mar. 22, 2011 International Search Report issued in International Patent Application No. PCT/IL2010/000574.

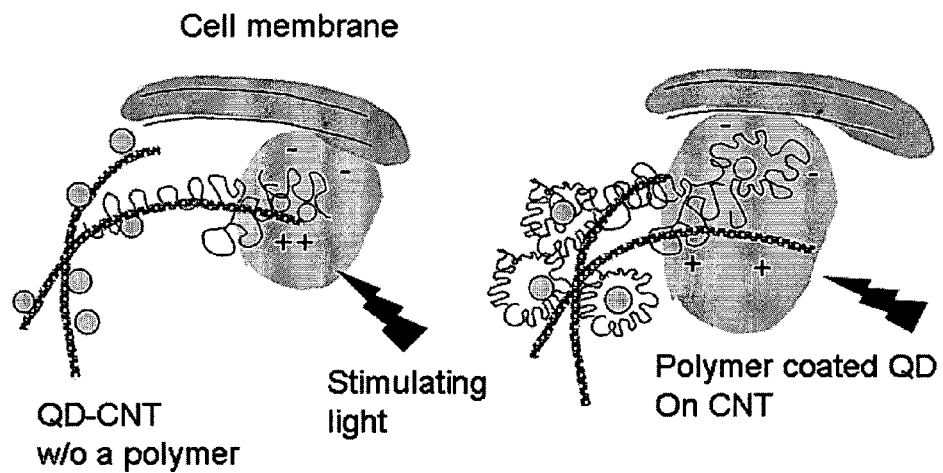
Fig. 1A
Fig. 1B
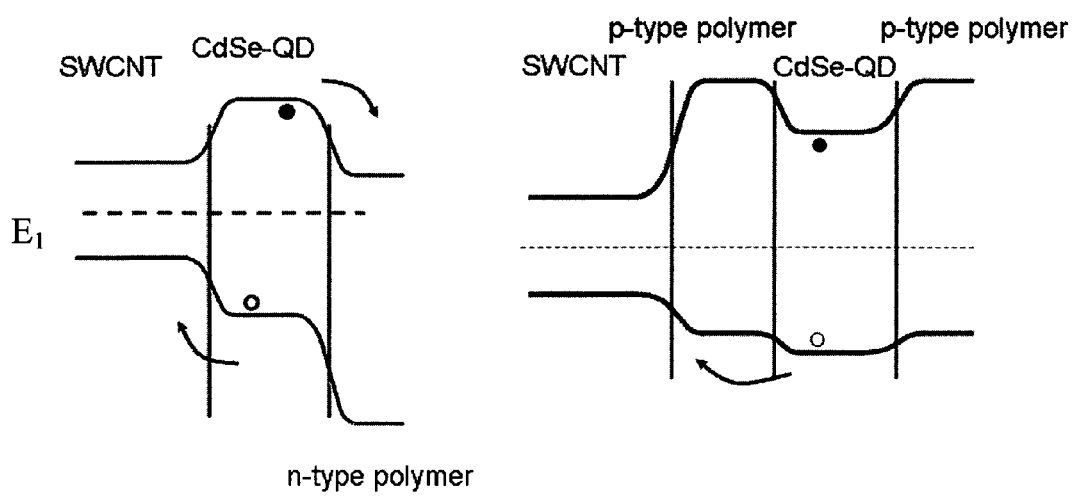
Fig. 2A
Fig. 2B

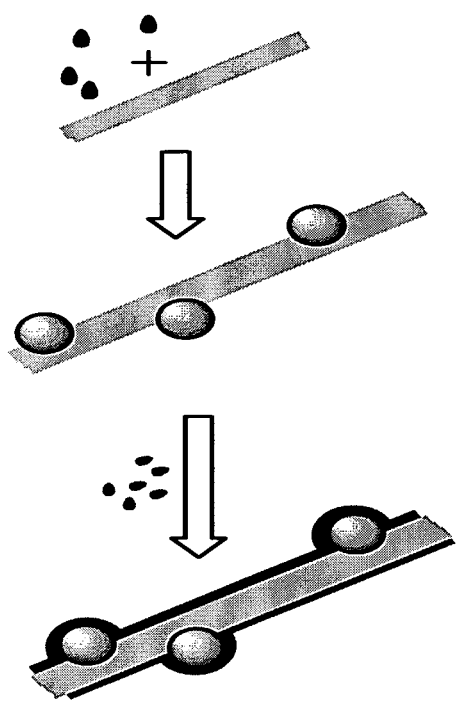
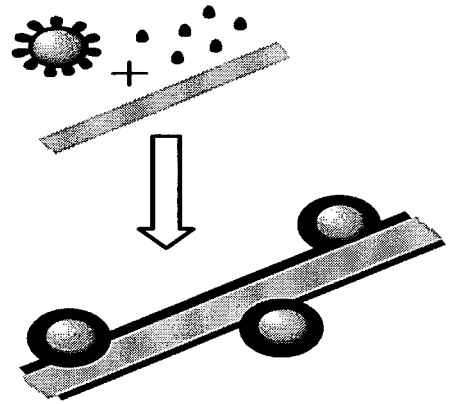
Fig. 5A
Fig. 5B

PHOTOELECTRICAL DEVICES FOR STIMULATING NEURONS

FIELD OF THE INVENTION

This invention relates to photoelectrical devices for stimulating neurons. More particularly, the invention relates to such devices utilizing carbon nanotubes.

REFERENCES

The following references are considered to be pertinent for the purpose of understanding the background of the present invention:
1. Feng Zhang, Li-Ping Wang, Martin Brauner, Jana F. Liewald, Kenneth Kay, Natalie Watzke, Phillip G. Wood, Ernst Bamberg, Georg Nagel, Alexander Gottschalk & Karl Deisseroth, Multimodal fast optical interrogation of neural circuitry, Nature, 446, 05744, (2007).
2. André Berndt, Ofer Yizhar, Lisa A Gunaydin, Peter Hegemann and Karl Deisseroth (2009), Bi-stable neural state switches, Nature Neuroscience 12(2):229-34.
3. T. C. Pappas, W. M. S. Wickramanyake, E. Jan, E, et al., Nanoscale engineering of a cellular interface with semiconductor nanoparticle films for photoelectric stimulation of neurons, Nano Lett., 7 513-519, 2007.
4. J. O. Winter, N. Gomez, B. A. Korgel, C. E. Schmidt, Quantum dots for electrical stimulation of neural cells, Proceedings of the SPIE—The International Society for Optical Engineering, 5705, 2005, 235-46 (2005).
5. Elena Molokanova, Joseph A. Bartel, Weiwen Zhao, Imad Naasani, Michael J. Ignatius, Joseph A. Treadway, A. Savtchenko, Quantum Dots Move Beyond Fluorescence Imaging, http://www.photonics.com/content/bio/2008/June/features/92282.aspx
6. A. P. Alivisatos, The use of nanocrystals in biological detection, Nat. Biotechnol. 22 (2004) 47-53.
7. J. E. Schroeder, I. Shweky, H. Shmeeda, U. Banin, A. Gabizon, Folate-Mediated Tumor Cell Uptake of Quantum Dots Entrapped in Lipid Nanoparticles, J. Controlled Release, 124, 28-34 (2007).
8. Winter, J. O; Liu, T. Y.; Korgel, B. A.; Schmidt, C. E. Recognition molecule directed interfacing between semiconductor quantum dots and nerve cells, Advanced Materials, v 13, n 22, Nov. 16, 2001, p 1673-1677+1656.
10. B. H. Juarez, C. Klinke, A. Konowski, H. Weller, Quantum dot attachment and morphology control by carbon nanotubes, Nano Lett. 7, 3564-3568 (2007).
11. E. Ben-Jacob and Y. Hanein, Carbon nanotube microelectrodes for neuronal interfacing, Journal of Materials Chemistry, 18, 5181-5186, 2008.
12. Electro-chemical and biological properties of carbon nanotube based multi-electrode arrays, Tamir Gabay, Moti Ben-David, Itshak Kalifa, Raya Sorkin, Ze'ev R. Abrams, Eshel Ben-Jacob and Yael Hanein, Nanotechnology, 18, 035201-035206 (2007).
13. Oren, R.; Sfez, R.; Korbakov, N.; Shabtai, K.; Cohen, A.; Erez, H.; Dormann, A.; Cohen, H.; Shappir, J.; Spira, M. E.; Yitzchaik, S., "*Electrically conductive 2D-PAN containing surfaces as a culturing substrate for neurons*" J. Biomater. Sci. Polymer Edn, 2004, 15(11), 1355-1374.
14. I. L. Medintz, H. T. Uyeda, E. R. Goldman, H. Mattoussi. Quantum dot bioconjugates for imaging, labelling and sensing, Nat. Mater. 4 (2005) 435-446.
15. M. David-Pur, S. Ben-Valid, S. Yitzchaik, and Y. Hanein, Very low impedance, micro/nano electrodes, Eurosensors 2008 XXII 354.

BACKGROUND OF THE INVENTION

Light activation of neurons is a growing field with applications ranging from basic investigation of neuronal systems to the development of new therapeutic methods. Several light activation approaches have been demonstrated using light sensitive membrane proteins [1, 2]. A different technique consists of using quantum dots (QDs) as artificial chromophores that can be placed at close proximity to cells and mediate electrical activation. Only few studies have indicated the potential of QDs in the realm of neuron photo-activation [3, 4]. It was demonstrated that HgTe particles could be used for light-induced activation of neurons in culture. The nanoparticles were deposited using a layer-by-layer (LBL) method on an ITO substrate and neuron culture was grown onto this surface. 532 nm laser illumination at 800 mW/cm$^2$ intensity was used (more than an order of magnitude higher than daylight intensity (~30 mW/cm$^2$)), resulting in successful neuronal stimulation. Invitrogen Corp. [5] has exploited the photoelectronic properties of QDs and developed a nanostructured biocompatible interface composed of stacks of semiconductor nanoparticles coated with an adhesion protein layer. The feasibility to interface with neurons through light activation has been demonstrated by [6, 7, 8].

General Description

Improving charge transfer efficiencies of photo-excited chromophores is at the focus of research conducted in the field of solar cell technology. Such solar cells include QD-coated electrodes embedded in electrolyte containing charge donors. In the presence of light, charges are injected from a QD matrix into the underlying support electrode and a direct current between a counter electrode in the solution and the QD-coated electrode is obtained. The manner by which the QDs are coupled to the electrode and to the solution are of utmost importance as the environment can affect resonance quenching or alternatively enhance charge transport processes. It is also likely that the effective band structure of the QDs is affected, giving rise to improved or suppressed photocurrent.

One particular approach to control these processes and to enhance the photocurrent is to use single wall carbon nanotubes as a linker between the QDs and the electrode. Organic coupling agents can be used to link the QDs to CNTs, requiring harsh chemical treatment of the CNTs to allow for their chemical functionalization. Another strategy for coupling QDs to CNTs uses a one-pot synthesis, in which CdSe QDs are grown in the presence of the CNTs leading to composites in which multiple QDs decorate the CNT along its axis. In this case, unlike the organic linking scenario, the QDs are closely adjacent to the CNTs, and this is expected to provide strong coupling between the two systems.

The present invention provides a novel photoelectrical device for efficient transmission of electrical signals to a neuron, so that the threshold for generating action potentials (impulses) is reached. This photoelectrical device comprises one or more charging units configured for coupling to and stimulating one or more neurons by charge accumulation, the charging unit comprising: a nanostructure based electrode having a surface, which has a predetermined developed surface area for coupling to a neuron and which carries a plurality of spaced-apart photosensitive regions (e.g. QDs) interfacing with a biocompatible macromolecule for tuning the relative energy levels between the photosensitive regions and the electrode, as well as for directing the spatial polarity of charge separation; the surface of the nanostructure based-electrode being thereby electrically chargeable and dischargeable in response to light excitation of the photosensitive regions, the charges stimulating the neuron when coupled to the surface, and thus enabling the transmission of electrical signals to the neuron.

In particular, the device of the present invention may be used for neuro-chip technology and more specifically for retinal implant technology.

Multielectrode arrays (MEAs) may be used to interface with neural assemblies, both for stimulation and recording purposes. In particular MEAs may be used for neural prosthetic devices to artificially restore impaired neural function (e.g. for vision, hearing and limb movement). One key issue is the biocompatibility of the electrode-tissue interface which must not only allow good electrical recording and stimulation performance, but also encourage strong cell adhesion and proliferation so that the electrodes remain effectively long-term coupled with the neurons. For optimal electrical coupling, the electrode surface must be as rough as possible so that it effectively enlarges the surface area. Independently, to achieve good biological coupling, the surface must be cell-adhesive. Interestingly, these two requirements can be attained concurrently if extremely rough and conducting surfaces are used [12]. Such surfaces can function both as excellent electro-chemical electrodes and substrates for neuronal growth [13].

The device is therefore activated (e.g. pumped) optically and the device output is in the form of an electric charge. It should be understood that although the device utilizes a photoelectric effect, the device is configured to use charge accumulation and not photocurrent generation as the device output.

In some embodiments, the nanostructure based-electrode includes carbon nanotubes (CNTs) having a predetermined developed surface area (i.e. specific outer surface) for coupling to a neuron (e.g. to obtain a strong neuron-carbon nanotubes affinity). It should be understood that the term "nanostructure electrode" has to be interpreted in a broadest manner in which the thickness of the electrode is in the order of micrometers and the diameter of the electrode is in the order of few micro-meters. The specific outer surface of the CNT enhancing the coupling of CNTs to neurons is characterized by a relatively long length of the nanotube and by the roughness of the outer surface. For example, the roughness of the electrode can be characterized by an electrode effective area 1,000 larger than the geometrical area of the electrode. Examples of such coupling and techniques for measuring the degree of coupling are described in Raya Sorkin, Alon Greenbaum, Moshe David-Pur, Sarit Anava, Amir Ayali, Eshel Ben-Jacob, and Yael Hanein, Process entanglement as a neuronal anchorage mechanism to rough surfaces. Nanotechnology, 20 (2009) 015101, which is incorporated herein by reference with respect to this specific example. Accordingly, the length of each nanotube is selected to be in the range of about 1 and 50 μm.

The CNTs operate as mediator to enhance the efficiency of the coupling between QDs and neurons. CNTs provide a very effective adhesive material for neuronal proliferation and facilitate both the strong coupling between the cells and the surface and the direct electrical recordings. The use of CNTs also contributes to the mechanical and electrical interfacing because they are chemically inert and robust against mechanical damage and easy to produce. Moreover, it should be noted that CNTs improve the performance of MEAs due to their many beneficial properties such as mechanical stability, chemical durability, good electrical conductance and their bio-compatibility.

It should be understood that CNTs possess unique electronic and mechanical properties. The CNT-based electronic device is dictated by its size and chirality to be either semiconducting or metallic, providing flexible tuning of the electrical properties. Moreover, CNTs are also highly neuronal-adhesive material and can serve as a good substrate for neural growth. Electrical stimulation of neurons grown on the CNTs in multi-electrode array (MEA) architecture is highly efficient.

QDs are versatile absorbing and emitting chromophores whose optical and electronic properties can be tuned by modifying the size, shape and composition of the particles. In particular, quantum confinement effects provide particles with band gaps covering the UV-VIS-NIR range. Moreover, QDs are photo and electro-active and can generate photocurrents. Diverse chemistries can be applied to the QDs surfaces to tailor them to be biocompatibility [14]. Some examples of QDs include nanoparticles selected from the periodic table group II-VI semiconductors and III-V semiconductors. Group II-VI semiconductors includes at least one of CdSe, CdTe, CdS, ZnSe, Group III-V semiconductors includes at least one of InP, GaAs. InP nanoparticles, in particular, offer very good spectral coverage in the visible range, and are therefore suitable for stimulation of neurons imitating retinal function.

In some embodiments, the quantum dot is selected from core/shell nanoparticles, heterostructured nanoparticles and a combination thereof. The core/shell nanoparticles include CdSe/CdS core/shell, CdSe/CdTe core/shell, CdSe/ZnS core/shell. The heterostructured nanoparticles include CdSe/ZnSe, InP/CdS, InP/ZnSe and other combinations. The heterostructured nanoparticles may have an elongated portion or being in the form of a nanorod.

Therefore, the present invention overcomes the low efficiency of conventional cell activation with light methods, by providing new efficient hybrid devices interfacing between chromophores and CNT to achieve efficient chromophore-neuron coupling including the cell-surface coupling as well as for electro-chemical interfacing efficiency.

It should be understood that to provide an efficient coupling between the carbon nanotubes and the QDs, the selection of appropriate chemical and electrical properties of the biocompatible macromolecules is critical. To this end, the biocompatible macromolecules and the QDs have to be linked by electrostatic or covalent interaction.

The biocompatible macromolecules are selected amongst polymers, biopolymers, macromolecules and other large molecules which, on one hand, are non-toxic, chemically inert, and substantially non-immunogenic to a living tissue, in vivo, ex vivo, in a human tissue or a tissue of a non-human, and, on the other, are conductive and capable of association with both the QDs and the CNTs.

The biocompatible macromolecules are used to tune the relative energy levels of the chromophores and the CNT as well as a means to direct the spatial polarity of charge separation.

The biocompatible macromolecule may be selected from polymers and biopolymers such as melanin, polyaniline (PANI), polypeptide, polypyrrole, polypeptide (linear, branched and looped conformations), poly-l-lysine, cellulose acetate, ethylene vinyl alcohol copolymer or any pre-polymer (e.g., a subset of lower molecular weight polymers or monomers, oligomers thereof), blend, mixture and hybrid thereof.

The macromolecule may be in the form of a polymer film (e.g. initially selected conductive polymer (CP) film or initially non-conductive converted into conductive during the device manufacture). The film may be located between the CNT and the QD (i.e. CP encapsulates the QD on top of the CNT) and may be associated therewith any one physical or chemical bond such as covalent, electrostatic, π-bonding, hydrogen-bonding interactions and van der Waals. The association of the biocompatible macromolecule should be selected or adapted to be either covalent or electrostatic interaction (association) with the QD and either π-bonding interaction or van der Waals interaction with the CNT. The interaction may involve bond formation between surface groups of the QD and the CNT having surface groups, which in some embodiments, include use of known bio-conjugation schemes such as avidin-biotin interaction. The macromolecule may alternatively be in the form of a coating on at least a portion of an outer surface of the QD (directly coupled to the CNT) and/or on any space region between the QDs on the CNT's surface. The thickness of such films is in the order of nanometers to ten nanometers and even to several microns.

As mentioned above, the polymer selected to be used in the device may not be inherently conductive, but may become conductive once the device is formed.

Generally, the device of the invention may be constructed directly from any one biocompatible macromolecule, e.g., biocompatible polymer, or indirectly through polymerizing, either in situ or prior to application, of pre-polymers, such as monomers or oligomers, which may or may not be in association (e.g., already bonded) with one or more of the QDs and/or the CNTs. Polymerization of the pre-polymer may be carried out employing any one method of polymerization. Non-limiting examples are electropolymerization, chemical polymerization photochemical polymerization and enzymatic polymerization, plasma polymerization, as known in the art. The polymerization may be initiated by anyone catalyst, as known in the art, or by actinic radiation. For example, where the biocompatible polymer is polyaniline, the monomer to be polymerized, e.g., via electropolymerization is aniline. In such a case, a charge-transport layer is used to couple the QDs and CNTs. The CNTs are wrapped with nanolayers of conducting polymers (CP) leading to a significant drop in the electrode impedance while preserving neurocompatibility.

In other embodiments, one or more of the photosensitive regions are encapsulated within a layer of a conductive polymer, such that the electrical contact between the photosensitive region and the nanostructure based-electrode is through the polymer.

The invention also provides a process for the manufacture of a photoelectrical device for stimulating a neuron. The method comprises selecting one or more carbon nanotubes to have a predetermined developed surface area for coupling to a neuron; the one or more carbon nanotubes being configured and operable as electrodes; associating a plurality of photosensitive quantum dots with each carbon nanotube; the obtained nanotubes associated with the photosensitive quantum dots being electrically chargeable and dischargeable in response to light excitation of the quantum dots, the charges stimulating the neuron when coupled to the surface; and coating with a polymer (as defined and characterized hereinabove) at least a portion of the carbon nanotube associated with the plurality of photosensitive quantum dots for tuning the relative energy levels between the photosensitive quantum dots and the carbon nanotube, as well as for directing the spatial polarity of charge separation.

The distribution of the QDs over the surface of the CNT may also depend, among other parameters, on the reaction conditions, as well as on the nature and chemical composition of the QDs, and on their size. The plurality of QDs may be arranged in a spaced-apart arrangement over at least one portion of the nanotube surface, where each QD or groups of two or more QDs (e.g. aggregates) are positioned at a certain distance from another QD. Alternatively, the QDs may be arranged in an unordered fashion over the surface of the CNT.

The association of the plurality of QDs with the CNTs, in any arrangement, may be achieved by depositing the QDs onto the carbon nanotubes, e.g., by electro-deposition. Alternatively, the QDs may be synthesized in the presence of the CNTs, thereby achieving direct association.

The invention further provides a process for manufacturing a photoelectrical device for stimulating neurons. The method comprises providing one or more photosensitive quantum dots coated with at least one pre-polymer (e.g., a monomer of a polymer); and polymerizing the pre-polymer (e.g., in situ) in the presence of a carbon nanotube selected to have a predetermined developed surface area for coupling to a neuron; the one or more carbon nanotubes being configured and operable as electrodes, the obtained nanotubes associated with the photosensitive quantum dots coated with polymer being electrically chargeable and dischargeable in response to light excitation of the quantum dots, the charges stimulating the neuron when coupled to the surface, thereby providing a photoelectrical device for stimulating neurons. In some embodiments, the pre-polymer is electropolymerizable. In this case, the step of polymerizing the pre-polymer comprises electropolymerization.

The invention is further concerned with a process of manufacturing of a photoelectrical device operable in biological conditions for stimulating neurons. The process comprises providing a substrate carrying at least one carbon nanotube, contacting the substrate with an aqueous or organic solution (or a mixture of organic solvents such as alcohols) comprising a plurality of charged (negatively or positively) quantum dots and with a solution (e.g. organic solution) containing charged biocompatible macromolecules (positively or negatively charged) or mixtures thereof; thereby to permit association between the nanotube, the quantum dots and a coating layer of the biocompatible macromolecules.

Therefore, there is provided a method of making a photoelectrical device for stimulating neurons. The method comprising: providing a substrate carrying one or more carbon nanotubes selected to have a predetermined developed surface area for coupling to a neuron; the one or more carbon nanotubes being configured and operable as electrodes; providing two solutions: a quantum dot solution containing charged photosensitive quantum dots; and a solution containing charged biocompatible macromolecules; the biocompatible macromolecules being configured for tuning the relative energy levels between the photosensitive quantum dots and the carbon nanotube, as well as for directing the spatial polarity of charge separation; and dipping the substrate first in one of the two solutions and then with the other solution to yield a nanotube carrying quantum dots and coated with biocompatible macromolecules, thereby providing a photoelectrical device for stimulating neurons.

In some embodiments, the substrate is first contacted with the aqueous solution comprising a plurality of charged quantum dots and thereafter with the solution containing charged biocompatible macromolecules.

In some embodiments, the substrate is first contacted with the aqueous solution comprising a plurality of charged quantum dots and thereafter is plasma polymerized with biocompatible macromolecules.

In some embodiments, the substrate is first plasma polymerized with biocompatible macromolecules, then contacted with the aqueous solution comprising a plurality of charged quantum dots and thereafter is plasma polymerized again with biocompatible macromolecules.

In other embodiments, the substrate is first contacted with the solution containing charged biocompatible macromolecules and thereafter with the aqueous solution comprising a plurality of charged quantum dots. The step of contacting between the substrate and the solutions may be performed by way of dipping, which may be repeated any number of times.

In some embodiments, the biocompatible macromolecules and the quantum dots are oppositely charged.

The present invention further provides a method of stimulating a neuron. The method comprises providing a photoelectrical device according to the present invention; placing the photoelectrical device in the vicinity of a neuron to be stimulated; and irradiating the device with light to thereby enable neuron stimulation.

In some embodiments, the method involves growing the neuron in the vicinity of the photoelectrical device.

In some embodiments, irradiating the photoelectrical device with light comprises selecting power irradiations and wavelength of light to control a stimulation level of the neuron.

The present invention further provides a method for retinal stimulation to create artificial vision keeping the output cells of the retina intact. The method comprises providing a photoelectrical device according to the present invention and placing the device in the vicinity of a neuron to be stimulated. Once signal indicative of input light (image) enters the retina through the device implanted in the retina, information is transmitted from the retina to the visual centers of the brain. Thus, the invention provides an artificial retinal device suitable to electrically stimulate the retina in the eye to produce artificial vision.

In this connection, it should be understood that degenerative retinal dystrophies are a major cause for blindness among the aging population. The common phenotype of these diseases is photoreceptor degeneration, whilst retinal ganglion cells (RGCs) (the output cells of the retina), remain intact and can still transmit information to the visual centers of the brain. Consequently, retinal implantable prosthetic devices can be used to stimulate RGCs directly, circumventing the degenerated photoreceptor pathway.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1A-1B are schematic illustrations of examples of photoelectrical devices according to the teachings of the present invention;

FIGS. 2A-2B are schematic energy level diagrams of the electron states corresponding to the photoelectrical devices of FIGS. 1A-1B respectively;

FIGS. 5A-5B are symbolic illustrations of a method of providing a charging unit of the kind described in FIGS. 4A-4B respectively;

DETAILED DESCRIPTION OF EMBODIMENTS

Reference is made to FIGS. 1A-1B, illustrating two different schematic configurations of photoelectrical devices in accordance with the teachings of the present invention. The photoelectrical device is operable to achieve charge separation for light activation of cells. FIGS. 2A-2B are the corresponding energy-level diagrams adjusted in relation to the vacuum level and equilibrated at the Fermi energy. The arrows indicate the charge carrier migration after excitation, leading to charge separation.

The photoelectrical device of FIG. 1A comprises a nanostructure based-electrode (e.g. carbon nanotube denoted CNT in the figure) carrying a plurality of spaced-apart photosensitive regions (e.g. Quantum Dots denoted QD in the figure). In operation, a light source (not shown) irradiates the charging unit, and excites the photosensitive regions. As a result an electron-hole pair is formed. The electron and the hole then migrate in opposite directions leading to charge separation. The charge separation creates an electric field, which stimulates the neuron.

The photoelectrical device of FIG. 1B comprises a nanostructure based-electrode (e.g. carbon nanotube denoted CNT in the figure) carrying a plurality of spaced-apart photosensitive regions (e.g. Quantum Dots denoted QD in the figure) and biocompatible macromolecules (e.g. conducting polymer film denoted polymer in the figure) continuously coating the photosensitive regions. Following the same process as in FIG. 1A, at excitation, an electron-hole pair is formed.

In some embodiments, the photosensitive regions include QDs. It should be understood that to facilitate the effective use of QDs to construct light activation in cells, the QDs have to be conjugated to additional elements which facilitate the following features: optimal charge transfer and efficient cell coupling. As the optical and opto-electro-chemical properties of QDs are very sensitive to their immediate neighboring environment, the exact choice of material used in conjunction with the QDs is crucial.

Figure 3:
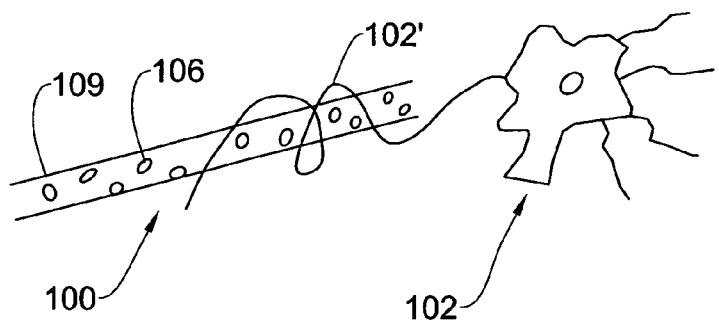
FIG. 3 is a schematic illustration of a charging unit for stimulating a neuron according to the teachings of the present invention.

Reference is made to FIG. 3 representing a schematic illustration of a charging unit 100 for stimulating a neuron 102. Neuron 102 is shown to include an axon 102', growing around a portion of the charging unit 100. Generally, various parts of the neuron can reside in the vicinity of the charging unit in various configurations. Charging unit 100 comprises a nanostructure based-electrode 104 and a plurality of spaced-apart photosensitive regions 106. The photosensitive regions 106 are spaced-apart on an outer surface of the electrode 104.

The nanostructure based-electrode 104 has a predetermined surface area for coupling to a neuron. This predetermined surface area is characterized by a certain roughness. The roughness may be measured by certain characteristic capacitance values of the electrode in the range of about 1 and 10 F cm$^{-3}$. The length of the nanostructure based-electrode is in the range of about 1 to 50 microns. The electrodes are configured with a specific geometry enabling the coupling to the neuron. In some embodiments, this specific geometry comprises a disk-like shape with an extending wire.

In some embodiments, the photosensitive regions 106 include biocompatible quantum dots. For example, the quantum dots include nanoparticles of InP, ZnSe.

Figure 4A:
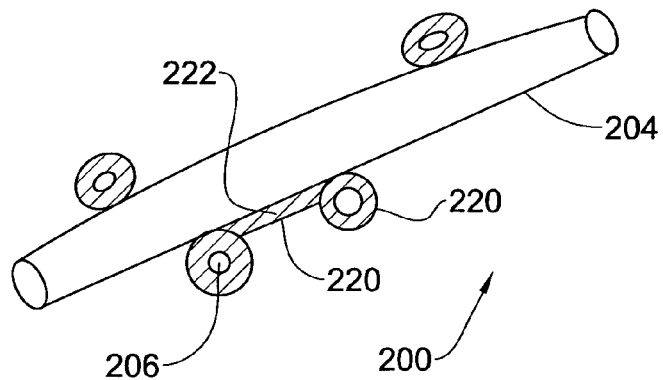
FIGS. 4A-4B are schematic illustrations of two possible configurations of the charging unit of the present invention comprising biocompatible macromolecules.

Reference is made to FIG. 4A representing a schematic illustration of a charging unit 200 comprising biocompatible macromolecules 220 for tuning the relative energy levels of the chromophores and the CNT, as well as for directing the spatial polarity of charge separation. The biocompatible macromolecules 220 may be a conductive polymer film. In this specific but non-limiting example, the film 220 is located between the electrode 204 and the photosensitive regions 206 (e.g. the film encapsulates the photosensitive regions on top of the electrode) and also coats a portion of an outer surface 222 of at least a portion of unit 200 in between the photosensitive regions 206. Optionally, the film 220 is made of a polymer coating which coats the entire outer surface of unit 200. In unit 200, photosensitive regions 206 are encapsulated in film 220 made of polymer, and thus, are electrically connected to electrode 204 only via film 220.

Figure 4B:
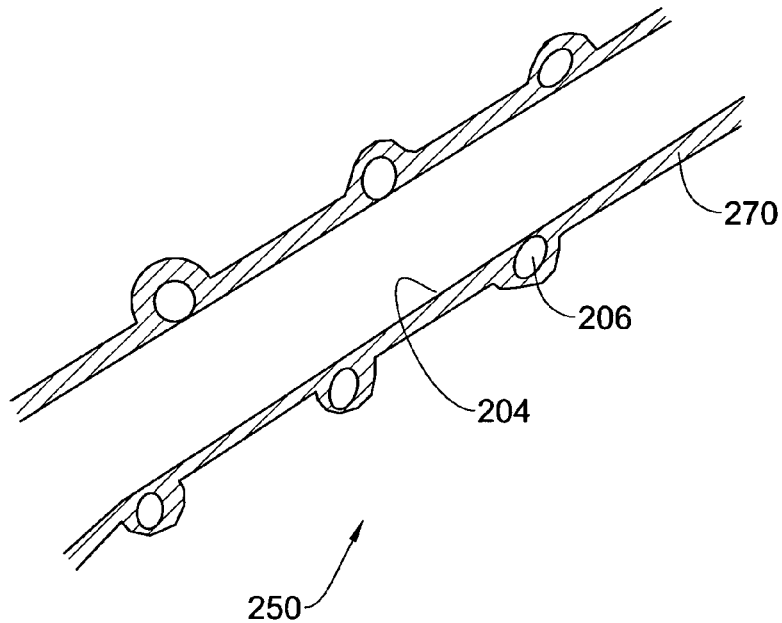

Reference is made to FIG. 4B representing another configuration of a charging unit 250 comprising biocompatible macromolecules 270, according to another embodiment. In this specific but non-limiting example, biocompatible macromolecules film 270 wraps (envelops) photosensitive regions 206 and electrode 204 together. In other words, the film coats the outer surface of the photosensitive regions 206 (directly coupled to the electrode) and the spaces between photosensitive regions 206 on the electrode surface. The photosensitive regions 206 are thus electrically connected directly to electrode 204.

In some embodiments, the quantum dots are synthesized in the presence of the carbon nanotubes to associate the quantum dots with the nanotubes.

Reference is made to FIG. 5A-5B representing illustrations of a method of providing a charging unit of the kind described in FIGS. 4A-4B respectively. In particular, FIG. 5A illustrates the charging unit of Type A formed by carbon nanotubes (CNTs) operable as the electrode, strongly coupled (directly) to a plurality of spaced-apart quantum dots. The outer surface of the QD and the spaces between QDs on the CN's surface are coated by a conductive film. The synthesis of the strongly coupled QD-CNT composites may be performed in a one pot approach [10]. For example, CdSe-CNT composites are provided by synthesizing CdSe QDs in the presence of the CNT. The quantum dots may also be selected from InP and ZnSe, to avoid the presence of potentially toxic Cd in the device. InP, in particular, offers very good spectral coverage in the visible range that is suitable for the retinal implant application.

In some embodiments, the CNT can be grown in a CVD system, and then the QDs are deposited onto the CNT. QDs deposition may be an electro-deposition. Another option is growing the QDs directly on the CNTs. QD can therefore be synthesized on CNT already grown in the CVD system directly onto substrates (quartz or silicon). The compatibility of the CNT substrates is controlled by appropriately selecting the synthesis conditions (temperature and solution). This synthesis yields to a charging unit of Type A kind.

FIG. 5B illustrates another configuration (Type B) of the charging unit formed by a carbon nanotube (CNT) operable as the electrode, coupled to a plurality of spaced-apart quantum dots. The conductive polymer may be made by in situ polymerizing monomers associated with quantum dots in the presence of carbon nanotubes to obtain a carbon nanotube associated with polymer-encapsulated quantum dots. Examples of electropolymerizable monomers include aniline. In this case, a charge-transport layer is used to couple the QDs and CNTs. The CNTs are wrapped with nanolayers of conducting polymers (CP) leading to a significant drop in the electrode impedance while preserving neuro-compatibility [15].

QDs ligand exchange with electro-polymerizable ligand followed by electro-polymerization on CNT containing MEA allows the formation of CNT-CP-QD nanocomposites. The CP may be selected from melanin and polyaniline. As an example, the organically soluble QDs out of the synthesis are first transferred to water via surface ligand exchange to mercaptopropionic acid (MPA). For incorporating with polyaniline, the negatively charged QDs are electrostaticly linked to the positively charged monomer (i.e., anilinium ions). Then, this system is electro-polymerized onto a MEA with CNTs.

An additional approach to form CNT-QD composites is to use Layer-By-Layer (LBL) deposition techniques. The charging unit is then made by dipping a CNT carrying substrate sequentially in two solutions, optionally, more than one time, so as to obtain a layer-by-layer preparation. One of the two solutions contains charged quantum dots, and the other—oppositely charged bio-macromolecules. In this specific example, the negatively charged QDs are electrostaticly assembled with positively charged bio-macromolecules such as poly-l-lysine or melanin. The MEA with the CNTs are dipped sequentially in solutions of the positive polymers and negative QDs. In this system, it is possible to change the nature of the binding polymer layer from insulating (poly-l-lysine) to conducting (melanin). This synthesis yields to a charging unit of Type B kind.

Figure 6:
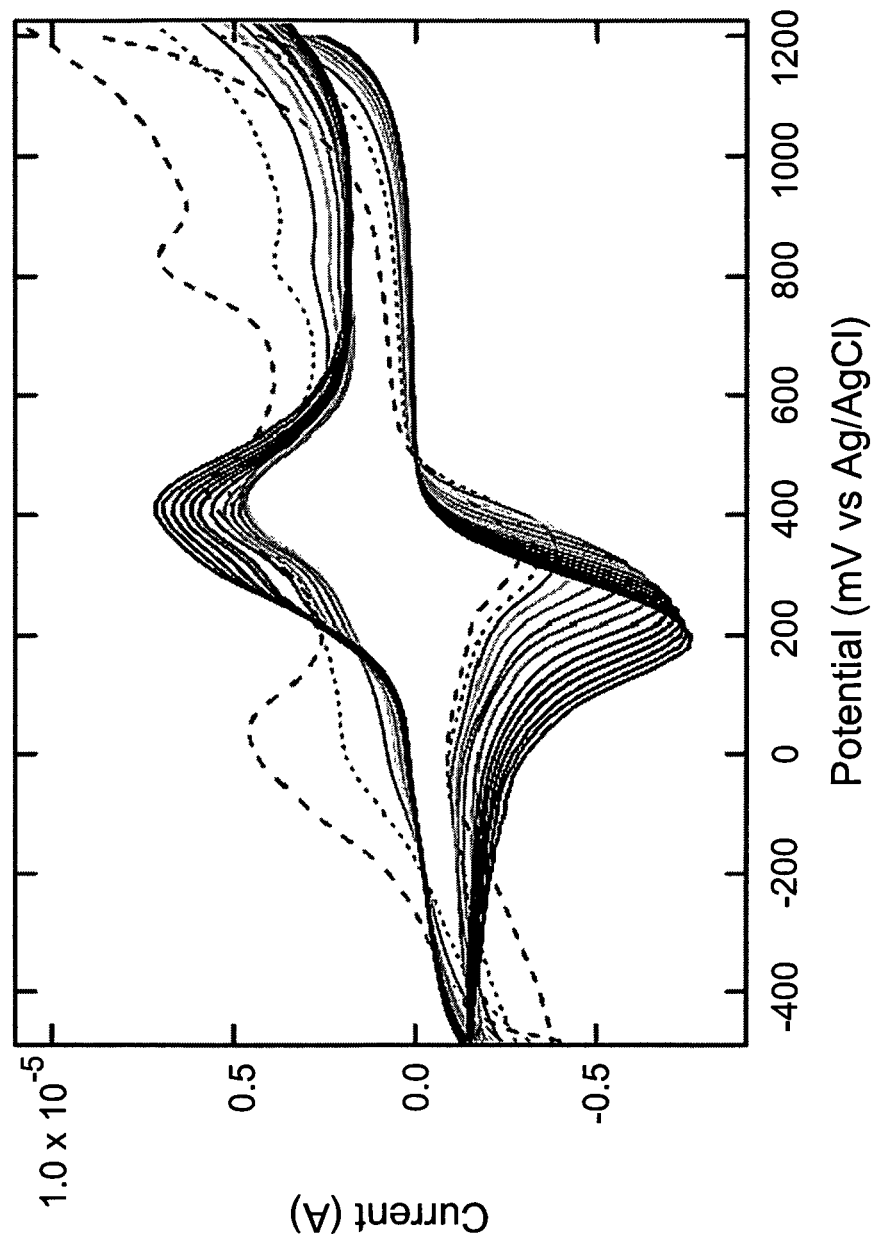
FIG. 6 is a Cyclic Voltammetry (CV) graph obtained during electrochemical coating of CNTs with a conductive polymer.

FIG. 6 illustrates a cyclic voltammetry graph obtained during electrochemical coating of CNTs with a conductive polymer. More specifically the CNT electrodes are coated by electrochemical polymerization of aniline. The voltammograms were performed in a voltage range of −0.5 to 1.2 V, scan rate of 20 mV/s and at 0.1 M aniline solution in distilled water (solution pH is 3.5). First and second scans are the dashed and dotted lines respectively. Consecutive scans are marked by increased amplitude. The graph shows efficient coating, with polymer thickness determined by the number of polymerization voltage cycles.

Figure 7C:
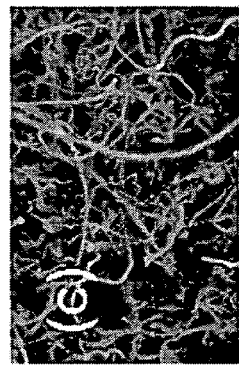
FIGS. 7C and 7D illustrate inspection of the electrodes before (7C) and after coating (7D)
Figure 7D:
Figure 7B:
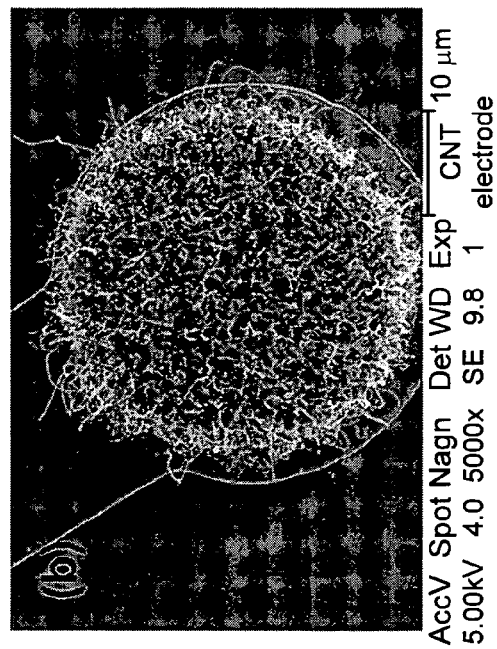
FIG. 7B is a high-resolution SEM (HRSEM) image of one of the electrodes in FIG. 7A.
Figure 7A:
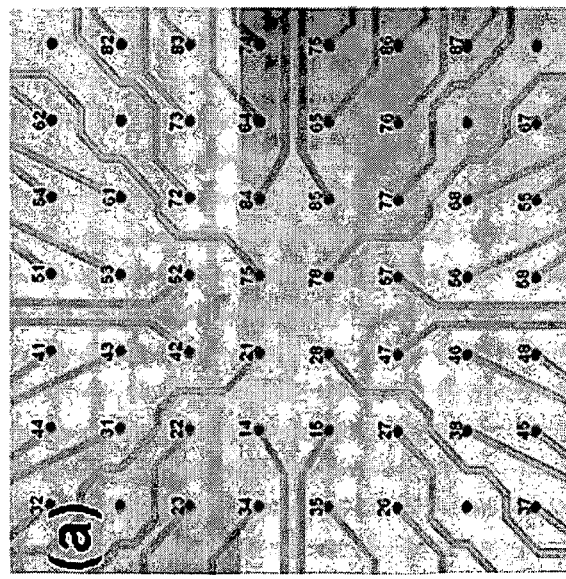
FIG. 7A is a photograph of a multi electrode array (MEA) of CNT electrodes.

FIG. 7A illustrates a multi electrode array (MEA) of CNT electrodes. In this specific example: a 60 CNT electrodes array. FIG. 7B is High-Resolution Scanning Electron Microscope (HRSEM) image of one of the electrode of FIG. 7A (30 µm CNT electrode). FIGS. 7C-7D illustrate inspection of the electrodes before (7C) and after coating (7D). The electrode illustrated in FIG. 7C is pristine CNTs. The electrode illustrated in FIG. 7D is CNT coated by polyaniline (PANI). The coated electrodes (FIG. 7D) appear thicker. Moreover, electrochemical characterization yields improved impedance of the electrode (i.e. better effective surface area leads to a lower impedance) corroborating the addition of a conducting polymer on the CNT surface.

Figure 8:
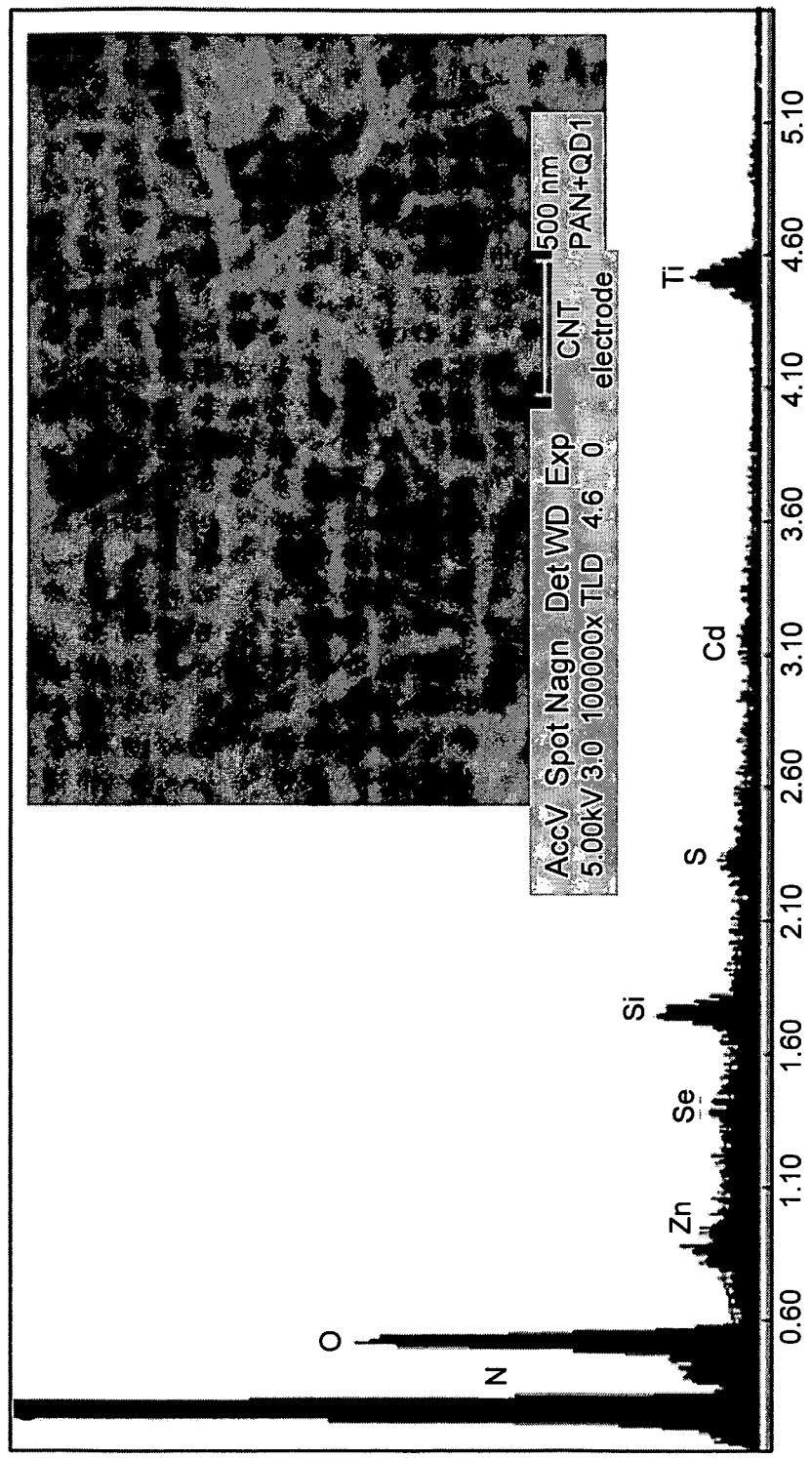
FIG. 8 shows Energy Dispersive X-ray (EDX) spectra of CNT coated with a conductive polymer and CdSe/ZnS quantum dots.

Implementation of the same coating procedure incorporating also QDs is shown in FIG. 8. The synthetic protocol is as described for configuration of TYPE B: an electrostatic assembly of anilinium ions on CdSe/ZnS core-shell system is followed by electro-polymerization in the presence of anilinium monomer. FIG. 8 is an Energy Dispersive X-ray (EDX) spectrum of the CNT electrode after coating by a conductive polymer (in this example Polyaniline (PAM)) wrapping CdSe/ZnS quantum dots. The inset is a SEM image of CNT-PANI-QD surface. As shown in the figure, Cd, Se, Zn, S, and N (of (PANI)) are detected. Evidence for light induced charging of the sample was also observed.

Figure 9A:
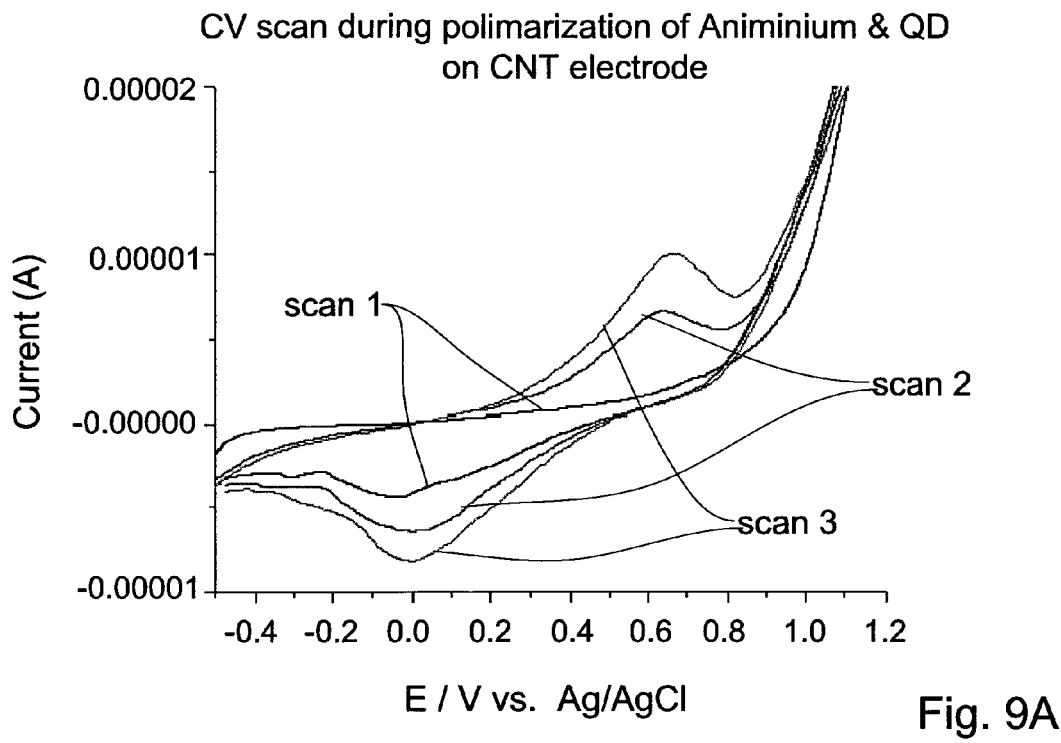
FIGS. 9A-9B shows CV measurement of CNT electrode during (9A) and after polymerization (9B) with CdSe/ZnS quantum dots.
Figure 9B:
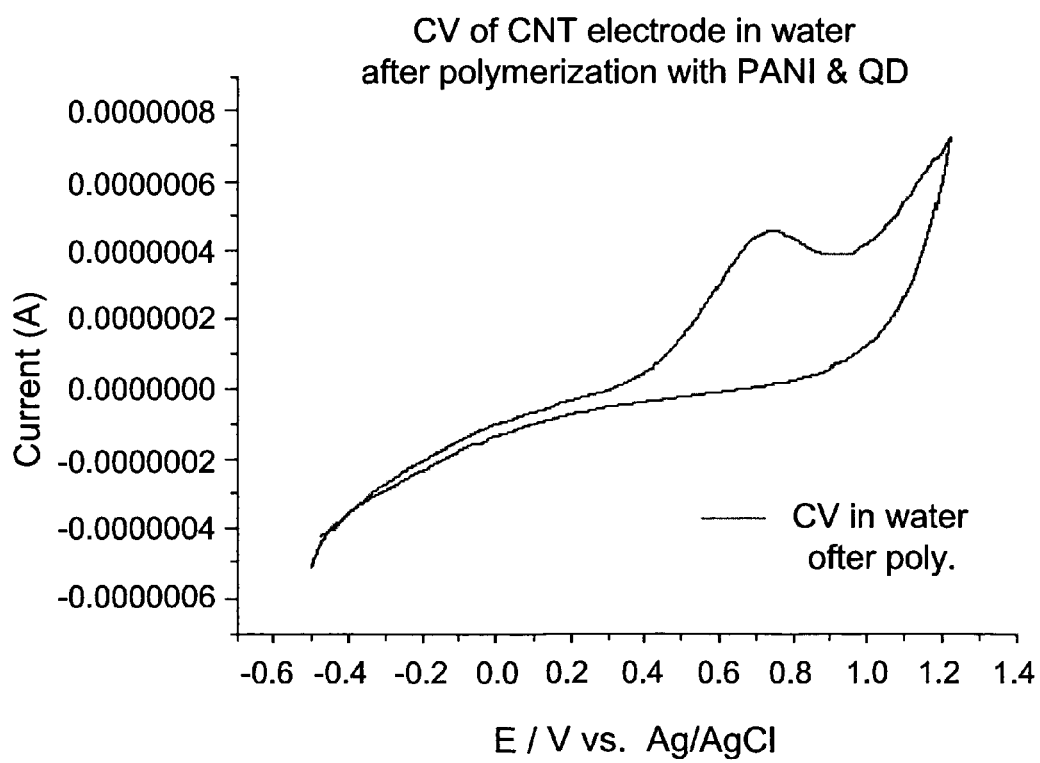

FIGS. 9A-9B shows a CV measurement of CNT electrode during (9A) and after (9B) polymerization with CdSe/ZnS quantum dots. In particular, FIG. 9A illustrates the CV of a CNT electrode during in situ polymerization with anilinium and CdSe—ZnS QD. The polymerization was performed in a potential range of −0.5-1.2V and scan rate of 0.05 mV/sec when the electrolyte is 0.1M aniline solution in pH~3. FIG. 9B illustrates CV of CNT electrode after polymerization with anilinium and CdSe—ZnS QD. The recording was performed in a potential range of −0.5-1.2V and scan rate of 0.005 mV/sec when the electrolyte is distilled water in pH~3.

CV measurements of CNT electrode during and after polymerization by PANI and CdSe—ZnS QD (FIGS. 9A-9B) reveal conspicuous hysteresis which is suggestive of charge separation as expected.

The inventors have also developed a multi electrode array (MEA) of CNT electrodes coated by CdSe QD using an LBL process as follows:

A MEA was set in water for 24 hours before the LBL process for providing a good wetting of CNTs. CdSe QDs (the cores only) were transferred to water by ligand exchange process. The water soluble ligand was selected to be mercaptoethanesUlfonate

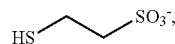

having a total size of about 3-4 nm, and a pH=10. A polycation solution was prepared from Poly(EthyleneImine)$_{AV}$ $_{Mw}$=25000 (PEI) 2 mg/ml. HCl was added to the charged polymer, changing the pH of the solution to 5. A LBL process was performed by dipping the MEA substrate in 5 ml of the poly-cation solution, or in a QD solution alternately, 8 min each layer, and dipping in water in between to wash off excessive PEI or QD not bound to surface. This process provides a—total of 5×2 layers for the MEA.

Figure 10A:
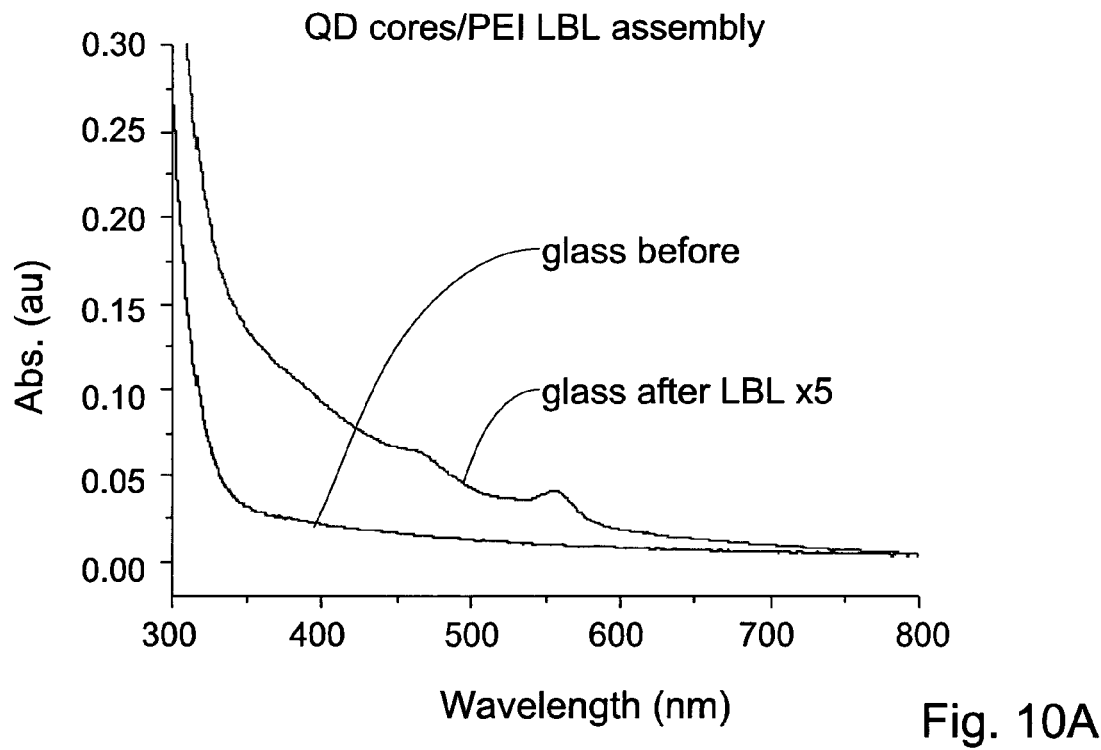
FIG. 10A shows QDs (coated on glass) absorption spectrum (semi-log graph) before and after the LBL process.
Figure 10B:
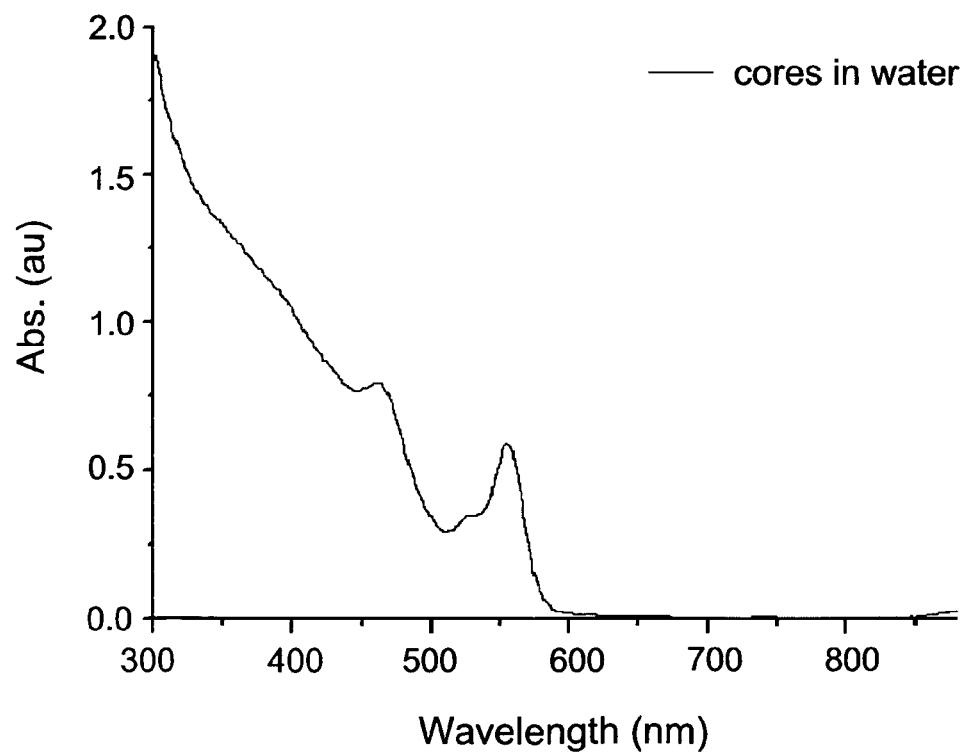
FIG. 10B illustrates absorption spectra for quantum dots with cores in water.

Reference is made to FIG. 10A illustrating QDs (coated on glass) absorption spectrum (semi-log graph) before and after the LBL process. FIG. 10B illustrates absorption spectra of quantum dots cores in water. As illustrated in FIG. 10A, the optical density (absorbance) at 553 nm for 5 layers of QDs on glass is 0.03 clearly indicating successful deposition of the layers using the above-described method.

For measuring photovoltage and photocurrent developed on these electrodes, when they are stimulated by irradiation with suitable wavelength and power, the following experimental set-up was used: open circuit photovoltage was measured by HP34401A DMM (1 MOhm input impedance, sampling rate 10 Hz, DC coupled) and short circuit photocurrent was measured by DL instruments 1212 Current Amplifier, under various power and wavelength irradiations by Mercury lamp (X-Cite 120 PC Q) focused by upright microscope (×40 lens), and was recorded by National Instruments DAQ, while the MEA is in physiological (Phosphate Buffered Saline—PBS) solution. The counter electrode was a wide CNT electrode (having a surface of few mm$^2$).

Figure 11:
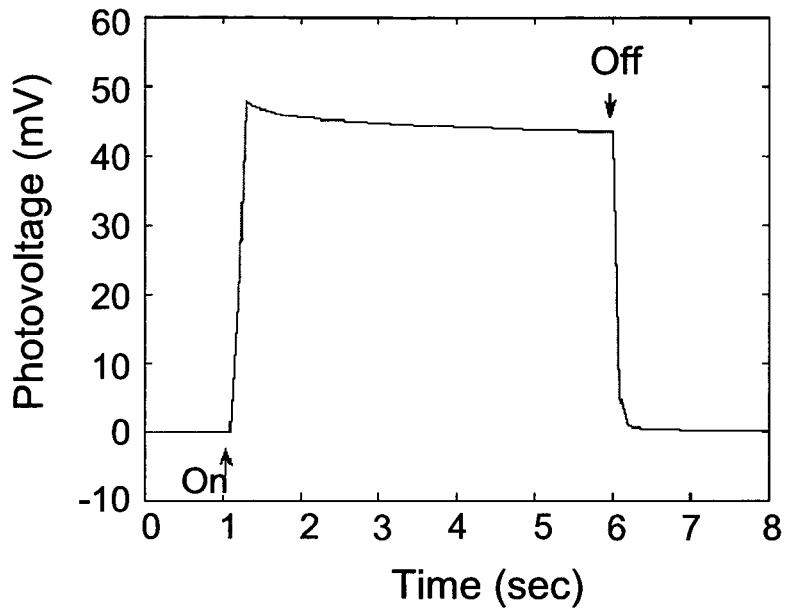
FIG. 11 shows an open circuit photovoltage measurement under near UV irradiation.

Reference is made to FIG. 11 illustrating an open circuit photovoltage measurement under near UV (360-375 nm) irradiation. As expected, the photoresponse of all electrodes is similar, due to the uniform manufacturing process, and shows a photovoltage of 44 mV. The irradiation power was selected to be 120 mW/cm$^2$. The electrodes diameter was selected to be 30 µm, and the irradiation beam diameter was selected to be 100 µm).

Figure 12:
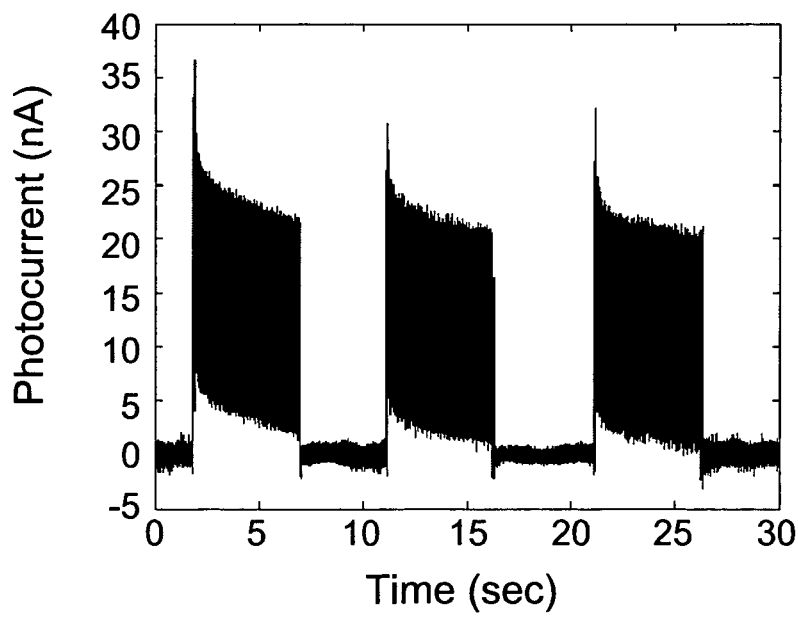
FIG. 12 shows short circuit photocurrent pulses measured under the same conditions as in FIG. 11.

Reference is made to FIG. 12 illustrating short circuit photocurrent pulses measured under the same conditions as in FIG. 11. The average photocurrent is about 13±2 nA (average and standard deviation—due to the different recording method of the photocurrent (higher sampling rate than the 10 Hz/DC coupling at the voltage measurements).

Figure 13B:
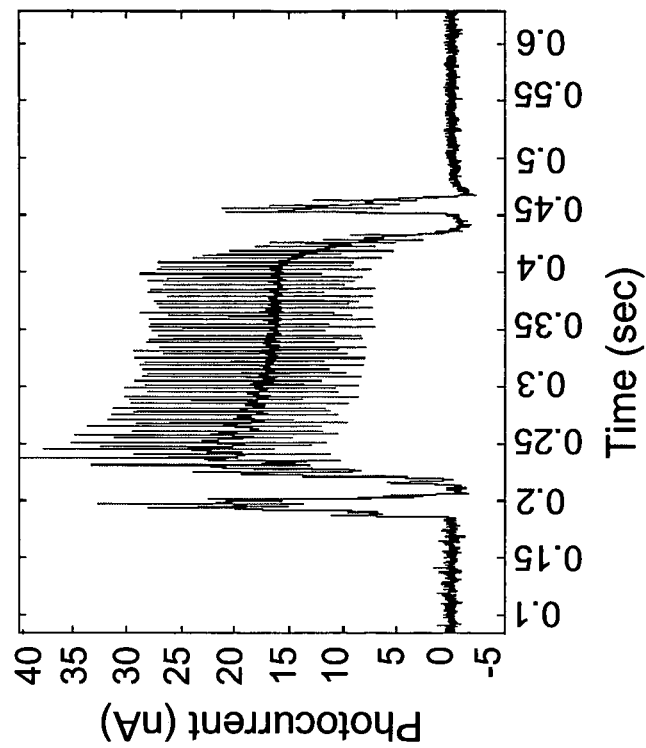
FIGS. 13A-13B show short circuit photocurrent pulses measured under an irradiation power of 3.75 mW/cm$^2$.
Figure 13A:
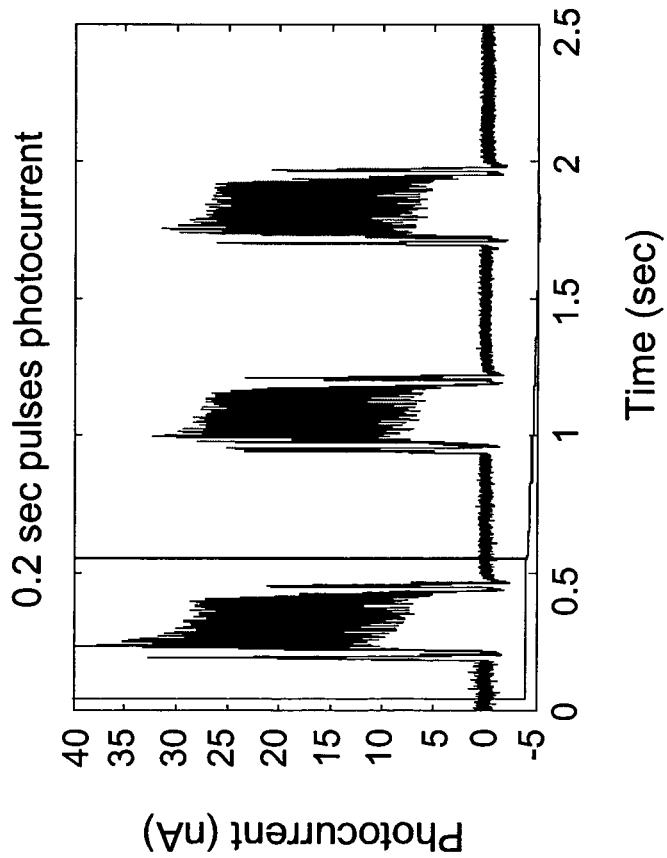

Reference is made to FIGS. 13A-13B illustrating short circuit photocurrent pulses measured under an irradiation power of 3.75 mW/cm$^2$. FIG. 13B illustrates an enlarged representation of one single pulse having a width time of 0.2 sec.

The maximum rise-fall time and the pulse height for the measurement illustrated in FIGS. 12 and 13A-13B are summarized in the following table:

| Irradiation power (mW/cm^2) | Max rise/fall time (ms) | Pulse height (nA) |
| --- | --- | --- |
| 120 ± 10 | 60 ± 5 | 13 ± 2 |
| 3.75 ± 0.25 | 30 ± 5 | 0.4 ± 0.1 |

Figure 14:
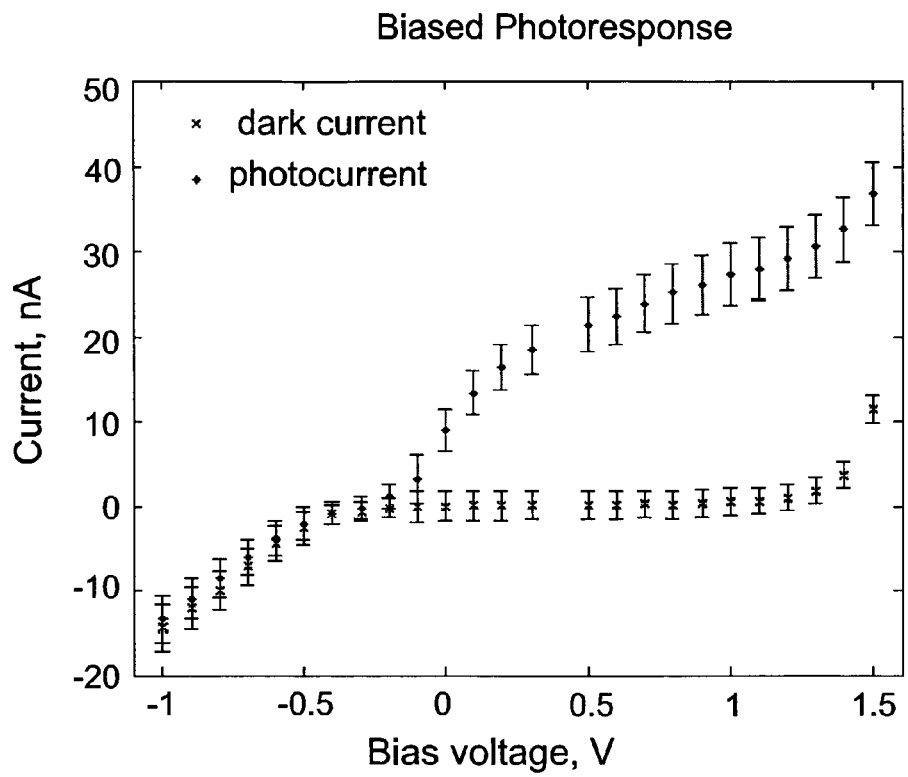
FIG. 14 shows measurement of a DC voltage biased dark and photocurrent (the bars represent standard deviation)

Reference is made to FIG. 14 illustrating the measurement of a DC voltage biased dark and photocurrent (the bars represent standard deviation). The photoresponse (=photocurrent minus dark current) begins at a bias voltage of −0.3V and comes to saturation at about 1.5V (from 1.3V the dark current become dominant and therefore the total current does not saturate). It seems that positive bias bends the energy bands, the charge carriers have more kinetic energy and the photocurrent increases, and vice versa. The negative bias of −0.3V rectifies the bands and blocks the charge carriers. The dark current is typical to such interface.

Figure 15:
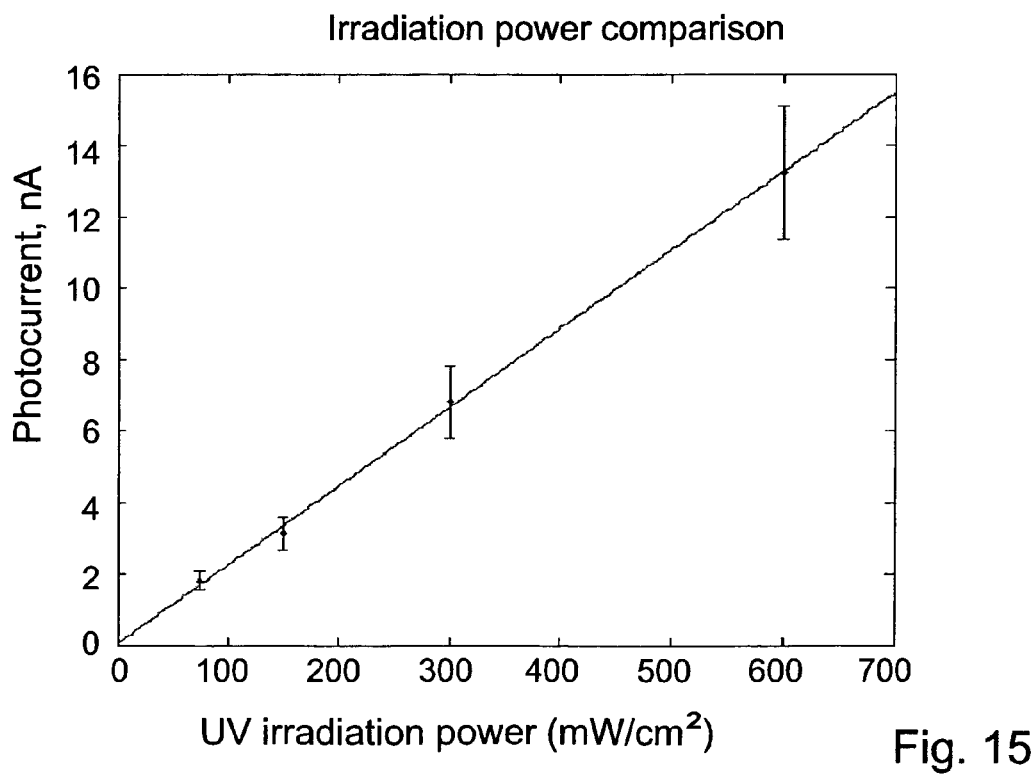
FIG. 15 shows photoresponse for different UV power irradiations.

Reference is made to FIG. 15 illustrating photoresponse to different UV power irradiations. As expected, the current is linearly proportional to the irradiation power, enabling the control of the stimulation level. The UV irradiation power range may be selected to be in the range of about 3.75-2000 mW/cm$^2$.

Figure 16:
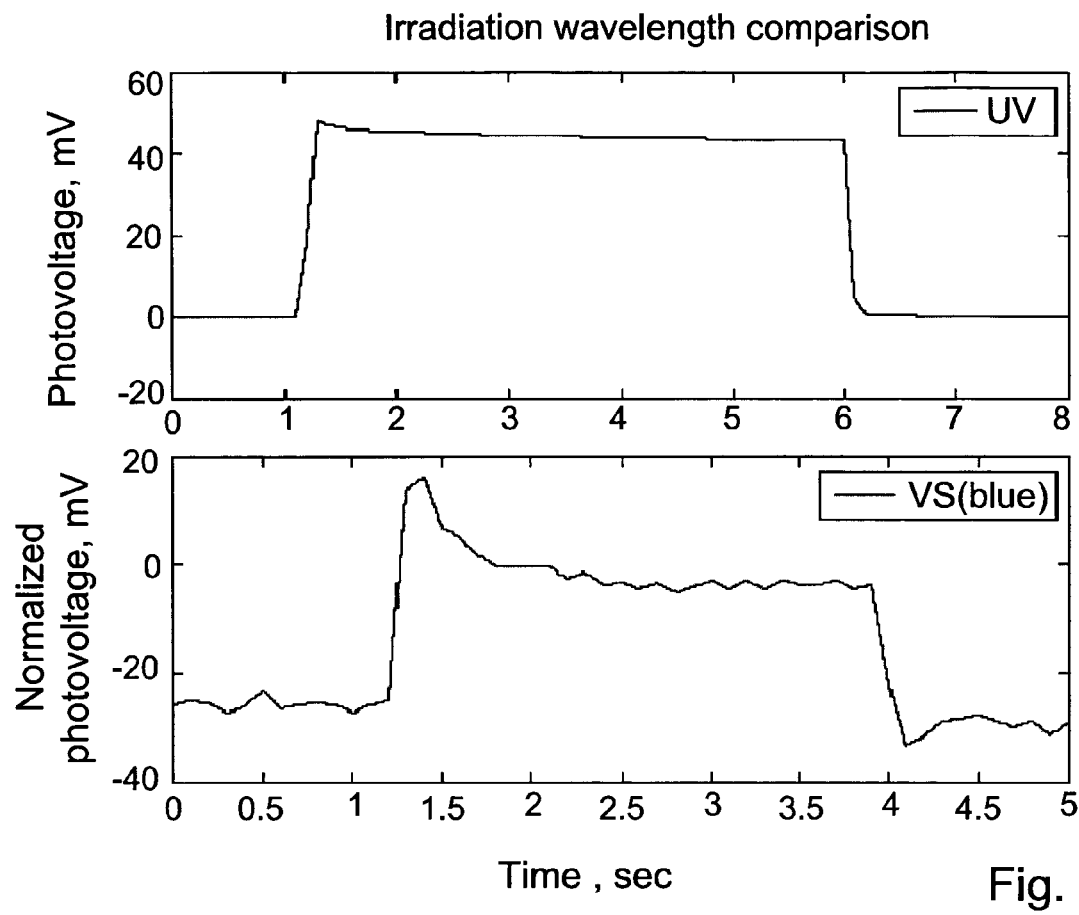
FIG. 16 shows photoresponse for different wavelength irradiations.

Reference is made to FIG. 16 illustrating photoresponse to different wavelength irradiations. In particular, the following wavelengths were selected to UV: 360-375 nm, blue: 410+440 nm. The photoresponse was normalized to an irradiation power of 120 mW/cm$^2$.

Figure 17:
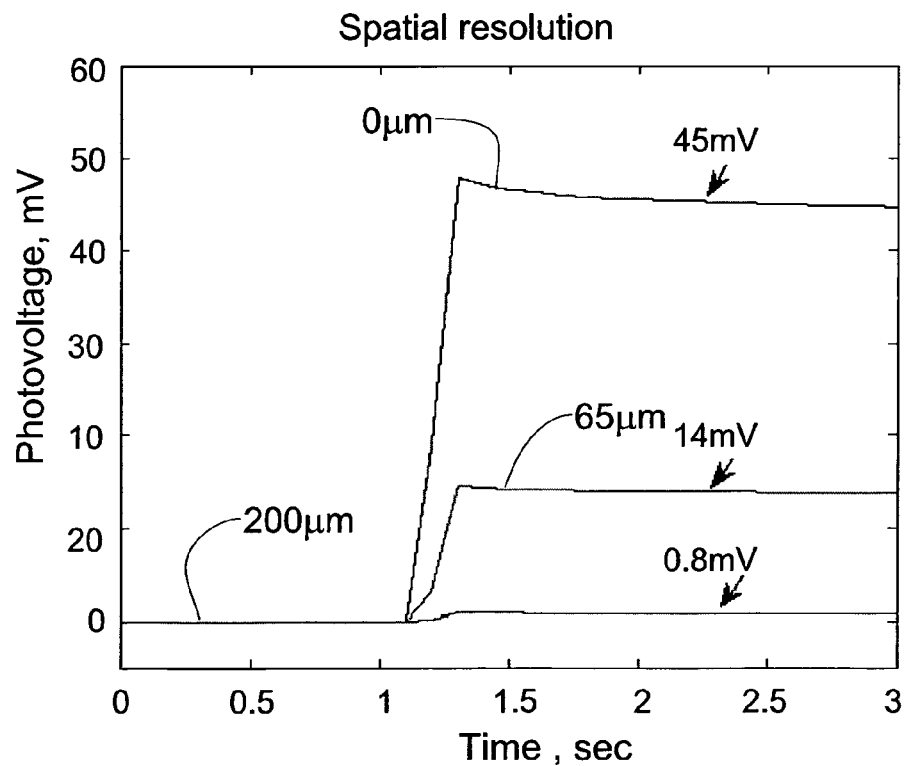
FIG. 17 shows spatial resolution photovoltage measurement in which the center of the irradiation beam is measured at different distances from the electrode (0 μm, 65 μm, 200 μm).

Reference is made to FIG. 17 illustrating spatial resolution photovoltage measurement in which the center of the irradiation beam is measured at different distances from the electrode (0 μm, 65 μm, 200 μm). The comparison between the 0 μm distance and the 200 μm distance demonstrates the capability of the system to stimulate only specific electrode without inducing noise to the recording electrodes, located at 200 μm from the specific electrode. The effect on adjacent electrodes (distanced at 65 μm) is 60 times lower, as illustrated in the figure.

Therefore, photovoltage and photocurrent are developed on these electrodes, when they are stimulated by irradiation with suitable wavelength and power, and their levels enable neurons stimulation.

The invention claimed is:

1. A photoelectrical device for transmitting electrical signals to a neuron, the device comprising: one or more charging units configured for coupling to and stimulating one or more neurons by charge accumulation, the charging unit comprising: a nanostructure based-electrode having a surface, which has a predetermined developed surface area for coupling to a neuron and carrying a plurality of spaced-apart photosensitive regions comprising quantum dots including nanoparticles selected from Group II-VI semiconductors and III-V semiconductors, said photosensitive regions interfacing with biocompatible macromolecules for tuning the relative energy levels between the photosensitive regions and the electrode, as well as for directing the spatial polarity of charge separation; said surface of the nanostructure based-electrode being thereby electrically chargeable and dischargeable in response to light excitation of said photosensitive regions, the charges stimulating the neuron when coupled to said surface, and thus enabling the transmission of electrical signals to the neuron.

2. A photoelectrical device of claim 1, wherein said nanostructure based-electrode includes one or more carbon nanotubes.

3. A photoelectrical device of claim 2, wherein said nanotubes are elongated, the length of each nanotube being selected to be in the range of about 1 μm to about 50 μm.

4. A photoelectrical device of claim 2, wherein said nanotubes are arranged in a multi-electrode array (MEA) architecture.

5. A photoelectrical device of claim 1, wherein said Group II-VI semiconductors includes at least one of CdSe, CdTe, CdS, ZnSe, and said Group III-V semiconductors includes at least one of InP, GaAs.

6. A photoelectrical device of claim 1, wherein a quantum dot is selected from core/shell nanoparticles, heterostructured nanoparticles and a combination thereof.

7. A photoelectrical device of claim 6, wherein said core/shell nanoparticles include CdSe/CdS core/shell, CdSe/CdTe core/shell, CdSe/ZnS core/shell.

8. A photoelectrical device of claim 6, wherein said heterostructured nanoparticles are characterized by at least one of the following: (a) include CdSe/ZnSe, InP/CdS, InP/ZnSe and other combinations, (b) have an elongated portion, (c) are in the form of a nanorod.

9. A photoelectrical device of claim 1, wherein one or more photosensitive regions are encapsulated by said biocompatible macromolecules.

10. A photoelectrical device of claim 1, wherein said biocompatible macromolecules are in the form of a polymer film.

11. A photoelectrical device of claim 10, wherein said polymer is characterized by at least one of the following: (i) electrically conductive, (ii) is selected from melanin, polyaniline (PANI), polypeptide, polycarbazole, and poly-l-lysine.

12. A photoelectrical device of claim 10, wherein said spaced-apart photo sensitive regions comprise quantum dots, said polymer film continuously coating an outer surface of at least a portion of said nanostructure based-electrode and at least a portion of each of said quantum dots.

13. A photoelectrical device of claim 1, wherein said quantum dots are electrically connected to the carbon nanotube via said biocompatible macromolecules.

14. A photoelectrical device of claim 1, wherein said quantum dots are directly electrically connected to the carbon nanotube.

15. A method of stimulating a neuron comprising: providing in the vicinity of the neuron a photoelectrical device of claim 1; and irradiating said photoelectrical device with light to thereby enable neuron stimulation.

16. A method of claim 15, wherein providing the photoelectrical device in the vicinity of the neuron comprises growing the neuron in the vicinity of the photoelectrical device.

17. A method of claim 15, wherein irradiating said photoelectrical device with light comprises selecting power irradiations and wavelength of light to control a stimulation level of the neuron.

18. A method of making a photoelectrical device for stimulating neurons, the method comprising: selecting one or more carbon nanotubes to have a predetermined developed surface area for coupling to a neuron; said one or more carbon nanotubes being configured and operable as electrodes; associating a plurality of photosensitive quantum dots including nanoparticles selected from Group II-VI semiconductors and III-V semiconductors with said carbon nanotubes; the obtained nanotubes associated with said photosensitive quantum dots being electrically chargeable and dischargeable in response to light excitation of said quantum dots, the charges stimulating the neuron when coupled to said surface; and continuously coating said obtained carbon nanotubes associated with photosensitive quantum dots with a polymer for tuning the relative energy levels between the photosensitive quantum dots and the carbon nanotube, as well as for directing the spatial polarity of charge separation.

19. A method of claim 18, wherein said providing one or more carbon nanotubes comprises synthesizing carbon nanotubes in a CVD system.

20. A method of claim 18, wherein said associating a plurality of quantum dots with said carbon nanotubes comprises at least one of the following: (1) depositing quantum dots onto the carbon nanotubes; (2) synthesizing the quantum dots in the presence of the carbon nanotubes.

21. A method of claim 18, wherein said associating a plurality of quantum dots with said carbon nanotubes comprises at least one of the following: depositing quantum dots onto the carbon nanotubes by electro-deposition; synthesizing the quantum dots in the presence of the carbon nanotubes.

22. A method of claim 18, wherein said polymer is selected from melanin, polyaniline and poly-l-lysine.

23. A method of claim 18, wherein said polymer is electrically conductive.

24. A method of making a photoelectrical device for stimulating neurons, the method comprising: providing one or more photosensitive quantum dots including nanoparticles selected from Group II-VI semiconductors and III-V semiconductors coated with monomers of a polymer; and in situ polymerizing said monomers in the presence of one or more carbon nanotubes selected to have a predetermined developed surface area for coupling to a neuron; said one or more carbon nanotubes being configured and operable as electrodes, the obtained nanotubes associated with said photosensitive quantum dots coated with polymer being electrically chargeable and dischargeable in response to light excitation of said quantum dots, the charges stimulating the neuron when coupled to said surface, thereby providing a photoelectrical device for stimulating neurons.

25. A method of claim 24, wherein said monomers are electropolymerizable.

26. A method of claim 24, wherein said in situ polymerizing comprises one of the following: polymerizing by electropolymerization; and polymerizing by plasma-polymerization.

27. A method of claim 25, wherein said monomers comprise aniline molecules.

28. A method of making a photoelectrical device for stimulating neurons, the method comprising: providing a substrate carrying one or more carbon nanotubes selected to have a predetermined developed surface area for coupling to a neuron; said one or more carbon nanotubes being configured and operable as electrodes; providing two solutions: a quantum dot solution including nanoparticles selected from Group II-VI semiconductors and III-V semiconductors and containing charged photosensitive quantum dots; and a solution containing charged biocompatible macromolecules; said biocompatible macromolecules being configured for tuning the relative energy levels between the photosensitive quantum dots and the carbon nanotube, as well as for directing the spatial polarity of charge separation; and dipping the substrate first in one of the two solutions and then with the other solution to yield a nanotube carrying quantum dots and coated with biocompatible macromolecules, thereby providing a photoelectrical device for stimulating neurons.

29. A method of claim 28, wherein said quantum dot solution is an aqueous solution or an organic solution.

30. A method of claim 28, wherein said solution is an organic solution.

31. A method of claim 28, wherein the biocompatible macromolecules and the quantum dots are oppositely charged.

32. A method of claim 28, wherein said dipping is repeated two or more times.

* * * * *